(12) United States Patent
Enggaard

(10) Patent No.: US 8,083,711 B2
(45) Date of Patent: Dec. 27, 2011

(54) INJECTION DEVICE WITH INTERNAL DOSE INDICATOR

(75) Inventor: Christian Peter Enggaard, Vejby (DK)

(73) Assignee: Novo Nordisk A/S, Bagsvaerd (DK)

( * ) Notice: Subject to any disclaimer, the term of this patent is extended or adjusted under 35 U.S.C. 154(b) by 324 days.

(21) Appl. No.: 11/665,485

(22) PCT Filed: Oct. 20, 2005

(86) PCT No.: PCT/EP2005/011288
§ 371 (c)(1),
(2), (4) Date: Nov. 13, 2007

(87) PCT Pub. No.: WO2006/045529
PCT Pub. Date: May 4, 2006

(65) Prior Publication Data
US 2008/0188797 A1  Aug. 7, 2008

Related U.S. Application Data

(60) Provisional application No. 60/626,250, filed on Nov. 9, 2004.

(30) Foreign Application Priority Data

Oct. 21, 2004 (EP) .................................... 04077901

(51) Int. Cl.
*A61M 5/30* (2006.01)
(52) U.S. Cl. ........................................... 604/68
(58) Field of Classification Search .................. 604/68
See application file for complete search history.

(56) References Cited

U.S. PATENT DOCUMENTS 6,235,004 B1   5/2001   Steenfeldt-Jensen
6,673,035 B1   1/2004   Rice et al.
6,899,699 B2 *  5/2005   Enggaard ..................... 604/246

FOREIGN PATENT DOCUMENTS

| EP | 0 338 806 B1 | 2/1994 |
| WO | WO 01/72361 | 10/2001 |
| WO | WO 02/053214 A1 | 7/2002 |
| WO | WO02053214 | 7/2002 |
| WO | WO 2004/078226 A2 | 9/2004 |
| WO | WO 2004078226 A2 * | 9/2004 |

* cited by examiner

Primary Examiner — Nicholas D Lucchesi
Assistant Examiner — Jason Flick
(74) Attorney, Agent, or Firm — Marc A. Began

(57) ABSTRACT

The present invention relates to an injection device comprising a housing, a resilient member adapted to provide a force in the axial direction of the injection device for ejecting a dose from the injection device. The injection device further comprises a dose setting member operatively connected to a dose indicator barrel positioned within the housing, the dose setting member and the dose indicator barrel being movable relative to each other and cooperating to set the dose to be ejected from the injection device. The dose indicator barrel undergoes, during dose setting, a combined rotational and translational movement within the housing and relative to the housing.

14 Claims, 4 Drawing Sheets

INJECTION DEVICE WITH INTERNAL DOSE INDICATOR

CROSS-REFERENCE TO RELATED APPLICATIONS

This application is a 35 U.S.C. §371 national stage application of International Patent Application PCT/EP2005/011288 (published as WO 2006/045529), filed Oct. 20, 2005, which claimed priority of European Patent Application 04077901.9, filed Oct. 21, 2004; this application further claims priority under 35 U.S.C. §119 of U.S. Provisional Application 60/626,250, filed Nov. 9, 2004.

FIELD OF THE INVENTION

The present invention relates to an injection device having an internally positioned dose indicator barrel adapted to display a dose of medicament to be ejected from the injection device.

BACKGROUND OF THE INVENTION

Various types of injection devices have been described over the years. However, injection devices formed as pen-type injection devices have attracted special attention over recent years.

For example, EP 0 338 806 discloses pen-like syringe incorporating a dose metering device. The pen is provided with a cap rotatable, with respect to a pen body, to a position representing the dose of medicament (for example insulin) to be injected. The rotation loads a torsion spring, which is prevented from unwinding by co-operating teeth. When the dose is to be injected, a trigger slide is moved to the left causing the toothing to come out of engagement. This disengagement allows the spring to unwind. The unwinding of the spring causes a drive sleeve, drive gear and a drive plunger to rotate. The drive plunger is formed with a quick pitch screw thread so that its rotational movement is accompanied by an axial movement which causes medicament to be discharged from a cartridge and injected through a needle.

EP 0 338 806 is based on a torsion spring. However, by applying a linear spring the axial movement of an integrated dose metering device could be made independent of the pitch screw threads on the plunger and the integrated dose metering device would be capable of rotating more than one revolution following a helical pattern.

U.S. Pat. No. 6,673,035 discloses a medical injector and medicament loading system for use therewith. The medicament loading system includes cap for a medicament cartridge. The cap has a post for causing movement of the cartridge stopper toward the seal when the cap engages the medicament cartridge to thereby eliminate adhesion between the medicament chamber and the stopper. The medical injector according to the present invention includes the medicament loading system, i.e. a cartridge assembly, a needle free syringe assembly, and a power pack assembly.

WO 02/053214 relates to a dose setting and expelling device comprising a drive member and a dose setting mechanism which simultaneously sets a given dose and stores the energy necessary for subsequently driving the drive member in order to expel a dose of medicine from an injection device. According to WO 02/053214 the dose setting mechanism allows adjustment in both directions, such that a given set dose can be reduced or cancelled by reversing the input motion, typically by rotating a setting member in a backward direction. Thus, WO 02/053214 discloses a simple dose setting and reverse mechanism. However, it is a disadvantage of the arrangement suggested in WO 02/053214 that the axial movement of an integrated dose metering device is dependent on the pitch screw threads on the plunger.

It is an object of the present invention to provide an injection device where the axial movement of the dose metering device is independent of the pitch of the threads on the plunger.

It is a still further object of the present invention to provide an injection device with a dose metering device allowing larger read-outs compared to known systems.

SUMMARY OF THE INVENTION

The above-mentioned objects are complied with by providing, in a first aspect, an injection device comprising
  a housing,
  a resilient member adapted to provide a force in the axial direction of the injection device, the force being necessary for ejecting a dose from the injection device, and
  a dose setting member operatively connected to a dose indicator barrel positioned within the housing, the dose setting member and the dose indicator barrel being movable relative to each other and cooperating to set the dose to be ejected from the injection device,
wherein the dose indicator barrel, during dose setting, undergoes a combined rotational and translational movement within the housing and relative to the housing. The dose indicator barrel (4) may engage a threaded portion of the housing (8).

In a first embodiment of the present invention, the dose setting member may engage the dose indicator barrel and the injection device may further comprise
  a piston rod having a threaded outer surface with a drive track arranged in a longitudinal direction of the outer surface of the piston rod,
  a drive member engaging at least part of the drive track of the piston rod and having a threaded inner surface cooperating with a threaded portion arranged on an outer surface of the dose indicator barrel, the drive member being adapted to drive and rotate with the piston rod during ejection of a dose from the injection device,
wherein the housing has a threaded portion cooperating with the threaded outer surface of the piston rod so that rotation of the piston rod results in an axial movement of the piston rod.

The drive track arranged in the piston rod may be an indentation in the longitudinal direction of the piston rod. Alternatively, it may also be a planar surface or two opposing planar surfaces as illustrated in for example FIG. 2.

In a second embodiment of the present invention, the dose setting member may engage the dose indicator barrel and the injection device may further comprise
  a piston rod having a threaded outer surface with a track arranged in a longitudinal direction of the outer surface of the piston rod,
  a drive member having a threaded portion cooperating with the threaded outer surface of the piston rod, and having a threaded inner surface cooperating with a threaded portion arranged on an outer surface of the dose indicator barrel, the drive member being adapted to rotate relative to the piston rod during ejection of a dose from the injection device,
wherein the housing engages at least part of the track of the piston rod so that rotation of the drive member results in an axial movement of the piston rod.

In a third embodiment of the present invention, the injection device may further comprise a piston rod having a threaded outer surface with a drive track arranged in a longitudinal direction of the outer surface of the piston rod, a resilient member housing being at least partly defined by the dose indictor barrel in combination with a main member, the dose indicator barrel and the main member being movable in relation to each other, the main member having a threaded portion cooperating with the threaded outer surface of the piston rod, a drive member operatively connected to the main member via a toothing so that the drive member is movable in relation to the main member during dose setting but rigidly connected to the main member during ejection of a dose from the injection device, the drive member engaging at least part of the drive track on the outer surface of the piston rod, wherein the housing has a threaded portion cooperating with the threaded outer surface of the piston rod so that rotation of the piston rod by the drive member results in an axial movement of the piston rod.

In the third embodiment, the injection device may further comprise an intermediate part engaging the dose setting member and the main member of the resilient member housing, the intermediate part being adapted to provided a biasing force to the drive member in a direction towards the toothing.

In a fourth embodiment of the present invention, the injection device may further comprise a piston rod having a threaded outer surface with a drive track arranged in a longitudinal direction of the outer surface of the piston rod, a resilient member housing being at least partly defined by the dose indictor barrel and a main member, a drive member operatively connected to the main member via a toothing in such a way that the drive member is movable in relation to the main member during dose setting but rigidly connected to the main member during ejection of a dose from the injection device, the drive member having threaded portion cooperating with the threaded outer surface of the piston rod, wherein the housing engages at least part of the track of the piston rod so that rotation of the drive member results in an axial movement of the piston rod.

The injection device according to the first and third embodiments may further comprise a locking member adapted to fixate the piston rod in such a way that no relative rotation of the piston rod and the housing is possible when the locking member is in its locking position. The injection device may further comprise a release button adapted for releasing the locking member from its locking position. The release button may be positioned in the distal half of the length of the injection device.

The injection device according to the second and fourth embodiment may further comprise a locking member adapted to fixate the drive member in such a way that no relative rotation of the drive member and the housing is possible when the locking member is in its locking position. The injection device may further comprise a release button adapted for releasing the locking member from its locking position, the release button being adapted to be released by a user of the injection device. The release button may be positioned in the distal half of the length of the injection device.

The resilient member may comprise a spring, such as a helical spring. The helical spring may be arranged coaxially with the piston rod.

BRIEF DESCRIPTION OF THE DRAWINGS

The present invention will now be described with reference to the accompanying figures wherein.

Figure 1:
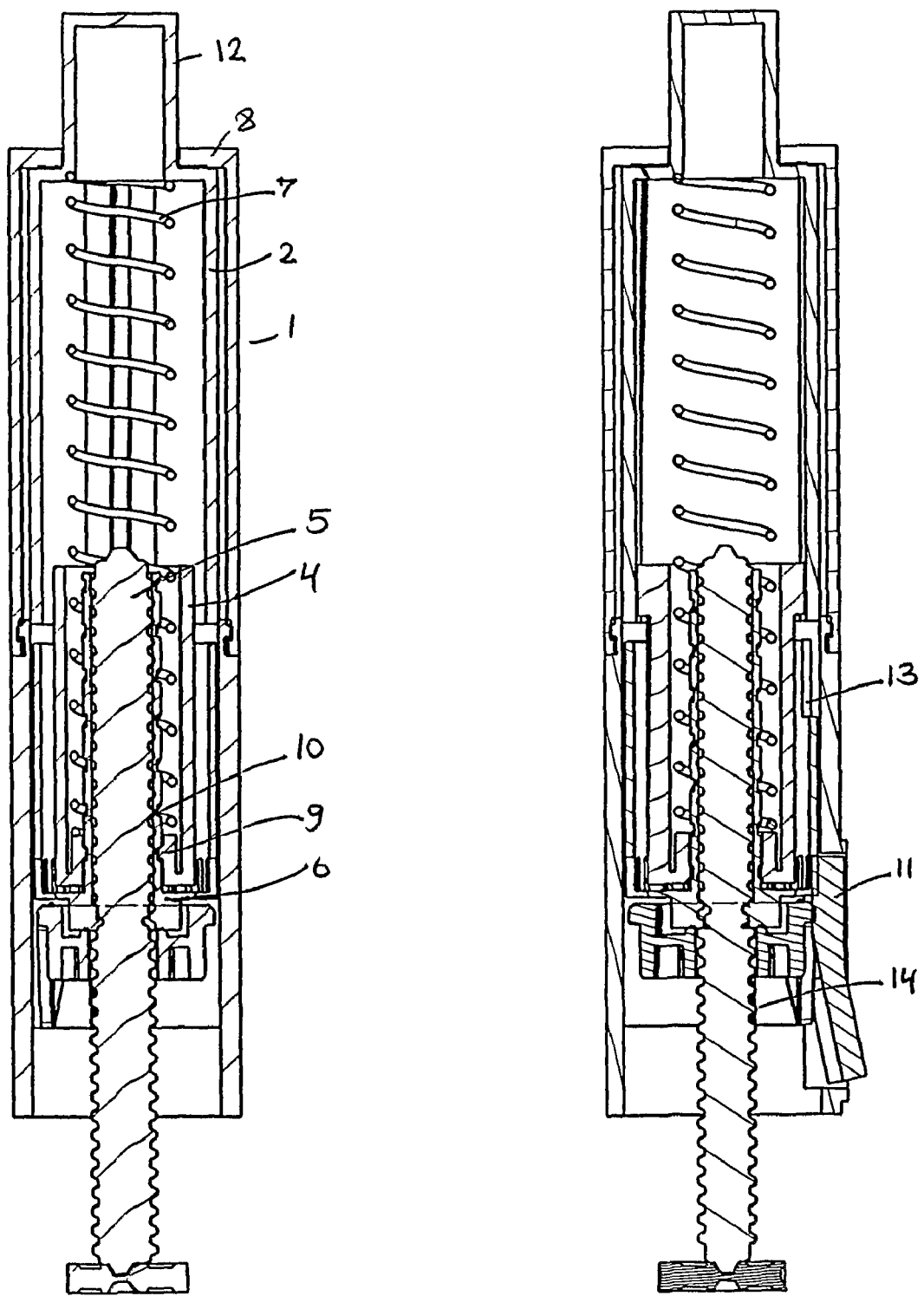
FIG. 1 is a cross sectional view of an injection device according to a first embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

FIG. 1 is a cross-sectional view showing half of an injection device 1 according to a first embodiment of the present invention. The injection device 1 comprises a dose setting member 2 being adapted to rotate about a centre axis of the injection device 1. It further comprises a dose indicator barrel 4, a threaded piston rod 5, a drive member 6 adapted to move the piston rod 5 along the centre axis, a helical spring 7 extending along and concentrically with the centre axis, and a housing 8.

The dose setting member 2 engages the dose indicator barrel 4 via a key/keyway connection. The key/keyway connection ensures that rotation of the dose setting member 2 about the centre axis causes rotation of the dose indicator barrel 4 about the centre axis, and advice versa. Furthermore, the key/keyway connection ensures that the dose setting member 2 and the dose indicator barrel 4 are slidably movable in relation to each other in a direction which is substantially parallel to the centre axis.

Similarly, the drive member 6 engages the outer threaded portion of the piston rod 5 via a threaded portion of the drive member.

The dose indicator barrel 4 is provided with a threaded portion 9 which engages a threaded portion 10 of the drive member 6.

The injection device 1 is further provided with a locking member 11 which may be switched between a locking state and an unlocking state. When the locking member 11 is in its locking state (as shown in FIG. 1) it prevents the drive member 6 from rotating about the centre axis. On the other hand, when the locking member 11 is in its unlocking state, the drive member 6 is free to rotate about the centre axis. The dose setting member 2 is connected to the housing 8 via a toothing connection 3. The toothing connection 3 allows the dose setting member 2 and the housing 8 to be rotationally movable in relation to each. However, the helical spring 7 provides an axial force to the dose setting member 2 and thereby to the toothing so that the dose setting member 2 stays in a set position.

The injection device of FIG. 1 is preferably operated in the following manner.

When a dose is to be set, the locking member 11 is switched to its locking state. In most cases, the locking state is the default position of the locking member 11. The user then causes the dose setting member 2 to rotate about the centre axis by turning a protruding part 12 of the dose setting member 2. Due to the key/keyway connection between the dose setting member 2 and the dose indicator barrel 4, the dose indicator barrel 4 is also caused to rotate about the centre axis.

Since the threaded portion 9 of the dose indicator barrel 4 engages the threaded portion 10 of the drive member 6, this rotation forces the dose indicator barrel 4 in a direction parallel to the centre axis and towards the protruding part 12 of the dose setting member 2. Thus, the dose indicator barrel 4 performs a sliding movement along the key/keyway connection between the dose setting member 2 and the dose indicator barrel 4. This movement causes the helical spring 7 to be compressed, thereby storing energy in the spring 7. Thus, the dose is set without causing any changes to the outer appearance of the injection device 1, including an outward movement of the dose setting member 2.

The dose indicator barrel 4 is provided with a set of numerals (not shown). As the dose indicator barrel 4 moves towards the protruding part 12 of the dose setting member 2, these numerals will be sequentially visible through a window 13 in the drive member 6, thereby indicating the dose which has been set. In order for the user of the injection device to view the numerals on the dose indicator barrel 4, the housing 8 is equipped with a belt-like window aligned with the window 13 in the drive member 6.

When the desired dose has been set, a needle (not shown) positioned opposite the protruding part 12 of the dose setting member 2 is inserted into a desired body part of the user. Then the locking member 11 is switched to its unlocking state, thereby allowing rotation of the drive member 6 about the centre axis. Due to the energy stored in the compressed helical spring 7, the dose indicator barrel 4 is forced towards its initial position, i.e. away from the protruding part 12 of the dose setting member 2. Via the threaded portion 10 and the threaded portion 9 of the dose indicator barrel 4, the drive member 6 is thereby caused to rotate about the centre axis, and due to a key/keyway connection between the housing 8 and the piston rod 5, the piston rod 5 will perform an axial movement away from the protruding part 12, thereby causing the desired and set dose to be ejected from the injection device 1.

Alternatively, the drive member 6 may comprise a key/keyway connection with the piston rod 5. Thus, the threaded portion of the drive member 6 will in this case be replaced by the key/keyway connection between the drive member 6 and the piston rod 5. In this case the piston rod 5 will rotate about the centre axis when the locking member 11 is switched to its unlocking state. The rotational movement causes the piston rod 5 to be moved in a direction parallel to the centre axis and away from the protruding part 12 of the dose setting member 2. The reason for this being that the threaded outer surface of the piston rod 5 engages a threaded portion of the housing 8. This movement will cause a dose to be ejected from the injection device 1.

When the dose has been ejected, the various parts of the injection device 1 are again in their initial position, except for the fact that the piston rod 5 has been moved in a direction away from the protruding part 12 of the dose setting member 2 due to the dose having been ejected. Even further, the angular position of the drive member 6 has changed whereby the "new" zero point has been angularly shifted relative to the housing 8. Thus, the injection device 1 is now ready for setting a new dose.

Figure 2:
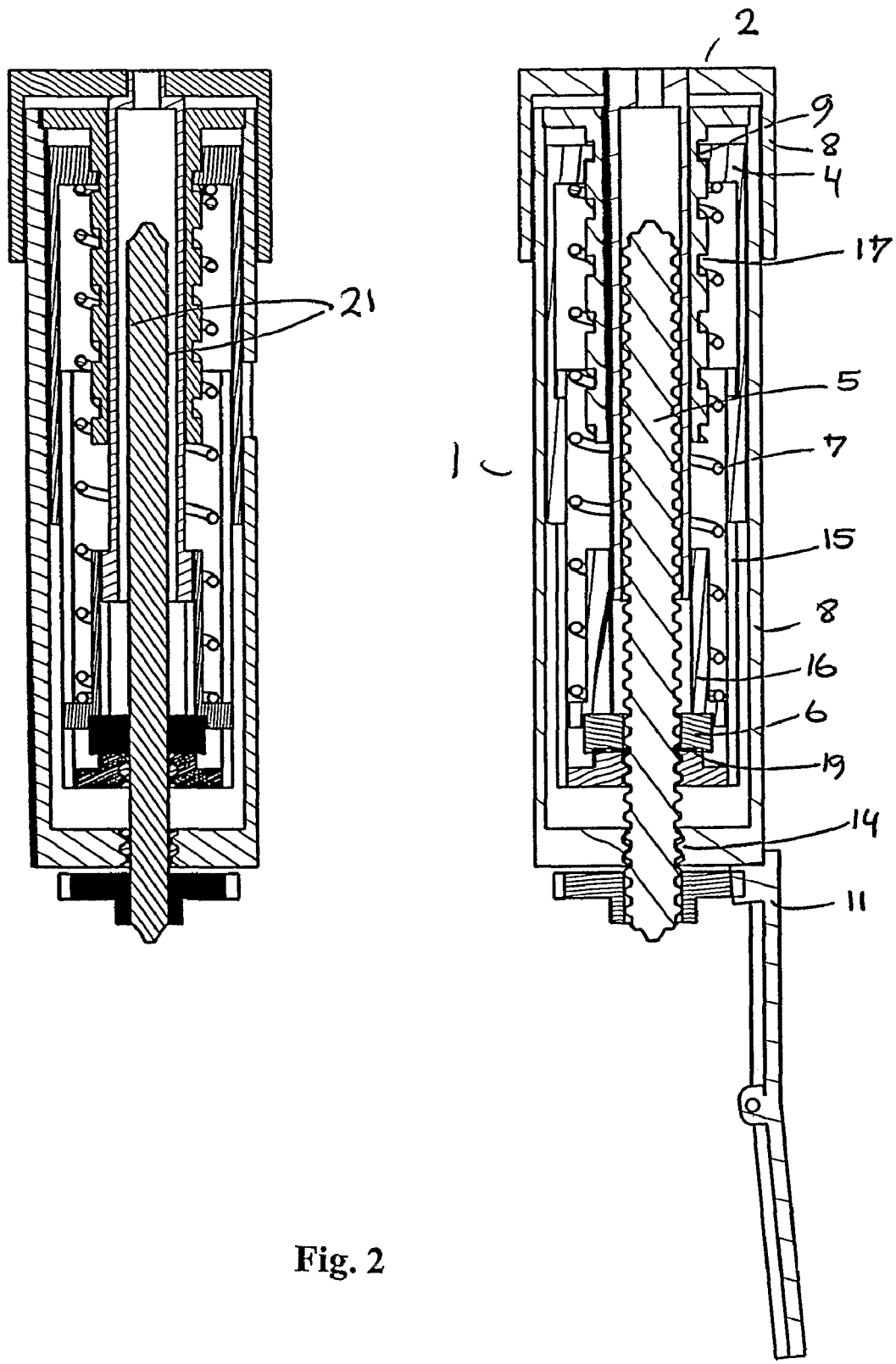
FIG. 2 is a cross sectional view of an injection device according to a second embodiment of the present invention.

FIG. 2 is a cross-sectional view showing half of an injection device 1 according to a second embodiment of the present invention. This embodiment is similar to the embodiment shown in FIG. 1, and like parts have therefore been provided with like reference numerals. Thus, the injection device 1 shown in FIG. 2 also comprises a close setting member 2 being adapted to rotate about a centre axis of the injection device 1. It further comprises a dose indicator barrel 4, a threaded piston rod 5, a drive member 6 adapted to rotationally drive the piston rod 5 about the centre axis, a helical spring 7 extending along and concentrically with the centre axis, and a housing 8.

The dose indicator barrel 4 engages a main member 15 via a key/keyway connection similar to the one described above. The drive member 6 is connected to the main member 15 via a toothing connection 19 allowing the drive member 6 and the main member 15 to be rotationally movable in relation to each. However, the helical spring 7 provides an axial force to the main member 15 and thereby to the toothing 19 so that the dose setting member 2 stays in a set position. An intermediate member 16 engages the dose setting member 2 via a key/keyway connection. It is also operationally connected to the main member 15 in such a way that when the intermediate member 16 rotates about the centre axis the main member 15 also rotates about the centre axis and vice versa. Finally, the main member 15 engages the threaded portion of the piston rod 5.

The dose indicator barrel 4 is provided with a threaded portion 9 which engages a threaded portion 17 of the housing 8.

The injection device 1 is further provided with a locking member 11 which may be switched between a locking state and an unlocking state. When the locking member 11 is in its locking state (as shown in FIG. 2) it prevents the piston rod 5 from rotating about the centre axis. On the other hand, when the locking member 11 is in its unlocking state, the piston rod 5 is free to rotate about the centre axis.

The drive track 21 arranged in the piston rod may be an indentation or groove in the longitudinal direction of the piston rod. Alternatively, it may also be a planar surface or two opposing planar surfaces.

The injection device 1 of FIG. 2 is preferably operated in the following manner.

When a dose is to be set, the locking member 11 is switched to its locking state which may be the default position of the locking member 11. The user then causes the dose setting member 2 to rotate about the centre axis by turning an outer part 18 of the dose setting member 2. The outer part 18 of the dose setting member 2 is a part which is positioned on the outside of the housing 8 as illustrated in FIG. 2. Due to the connections between the various parts of the injection device 1 described above, the rotation of the dose setting member 2 about the centre axis causes the intermediate member 16, the main member 15 and the dose indicator barrel 4 to be rotated about the centre axis. The drive member 6 is not rotated due to the toothing connection between the drive member 6 and the main member 15. Since the threaded portion 9 of the dose indicator barrel 4 engages the threaded portion 17 of the housing 8, and due to the main member 15 engaging the threaded part of the piston rod 5, the dose indicator barrel 4 and the main member 15/intermediate member 16 will be moved towards each other. This causes the helical spring 7 to be compressed, thereby storing energy in the spring 7. Thus, as it is the case in the embodiment shown in FIG. 1, the dose is set without causing any changes to the outer appearance of the injection device 1.

The dose indicator barrel 4 is provided with a set of numerals (not shown). As the dose indicator barrel 4 moves away from the outer part 18 of the dose setting member 2, these numerals will be sequentially visible through a window 13 in the housing 8, thereby indicating the dose which has been set.

When the desired dose has been set, actions similar to the ones described above in connection with FIG. 1 are performed. However, when the locking member 11 is switched to its unlocking state the following happens. The piston rod 5 is now free to rotate about the centre axis. Due to the energy stored in the helical spring 7, the dose indicator barrel 4 and the main member 15/intermediate member 16 will be forced away from each other. Due to the threaded portion 9 engaging the threaded portion 17 of the housing 8, the dose indicator barrel 4 is thereby rotated about the centre axis in a rotational direction which is opposite to the direction in which it was rotated when the dose was set. This, in turn, will cause the main member 15, the intermediate member 16 and the dose setting member 2 to rotate about the centre axis in the same direction. Due to the toothing connection between the main member 15 and the drive member 6, the drive member 6 is also caused to rotate about the centre axis, and due to the key/keyway connection between the drive member 6 and the piston rod 5, the piston rod 5 is also caused to rotate about the centre axis. The threaded part of the piston rod 5 engages a threaded portion 14 of the housing 8. Therefore the rotational movement causes the piston rod to be moved in a direction parallel to the centre axis and away from the outer part 18 of the dose setting member 2, thereby causing the desired and set dose to be ejected from the injection device 1.

As described above, the injection device 1 is now ready for setting a new dose.

Figure 3:
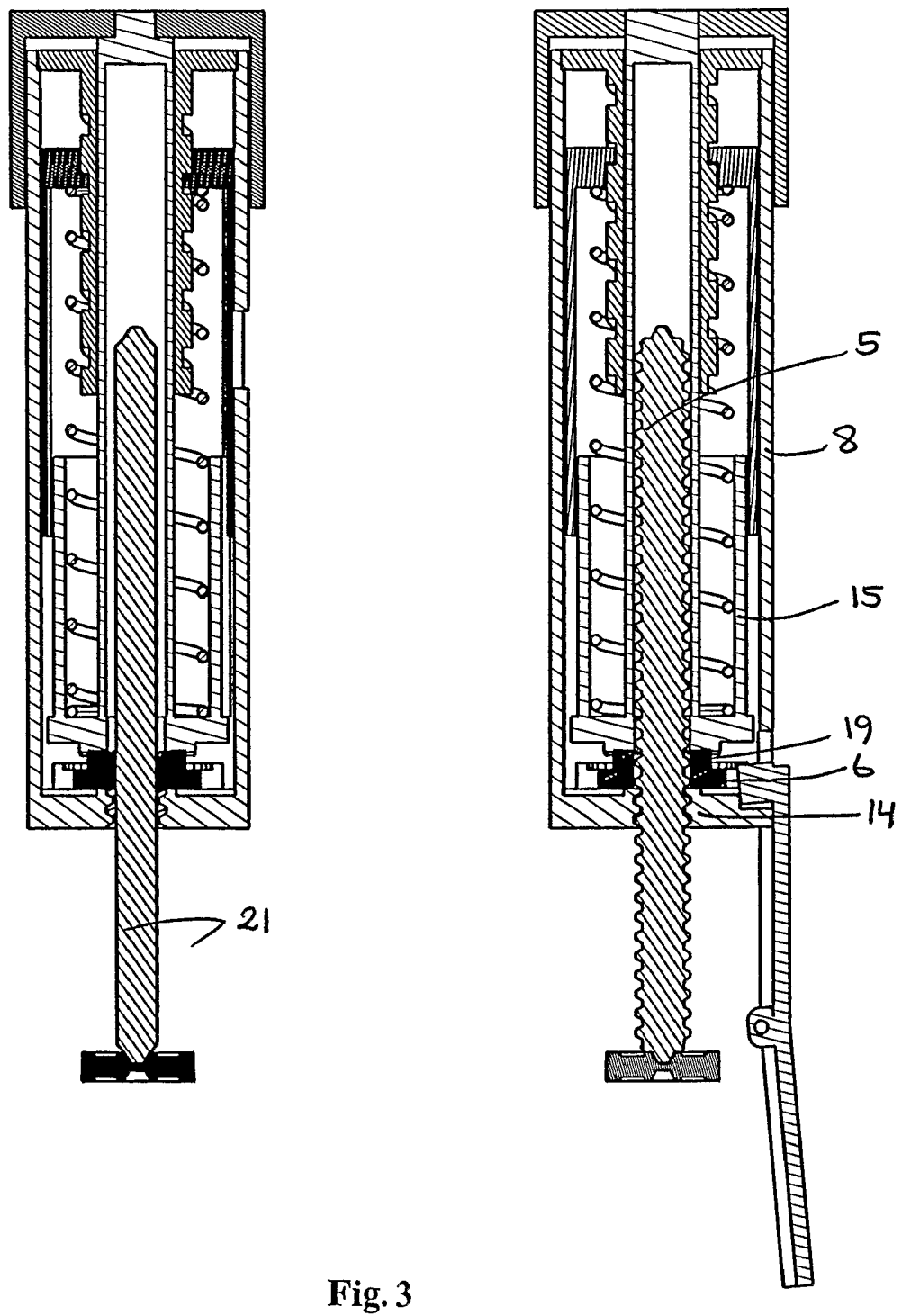
FIG. 3 is a cross sectional view of an injection device according to a third embodiment of the present invention.
Figure 4:
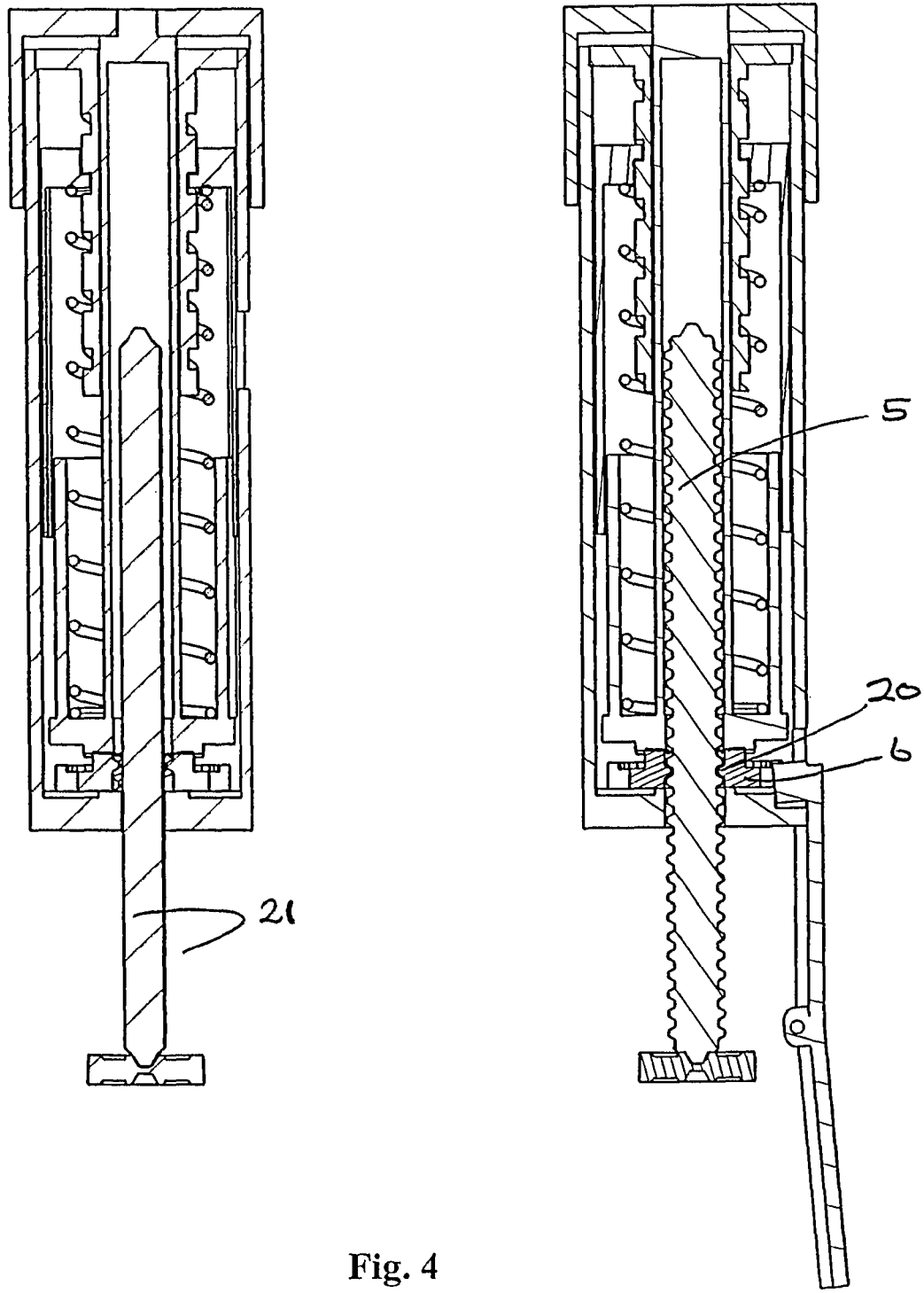
FIG. 4 is a cross sectional view of an injection device according to a fourth embodiment of the present invention.

Alternative embodiments are shown in FIGS. 3 and 4. Compared to the second embodiment shown in FIG. 2, the intermediate member 16 has been omitted whereby the mechanical design of the injection device has been significantly simplified. In FIGS. 3 and 4 the main member 15 is operatively connected to drive member 6 via toothing 19. In FIG. 3 the threaded outer surface of the piston rod 5 engages with a threaded portion 14 of the housing 8, whereas in FIG. 4 the threaded outer surface of the piston rod 5 engages with a threaded portion 20 of the drive member 6.

Thus, in the embodiment shown in FIG. 1 as well as in the embodiment shown in FIG. 2, the ejection of the dose is actually effected by the energy stored in the helical spring 7 when setting the dose, and the only effort required from the user of the injection device 1 in order to cause the ejection is the switching of the locking member 11 from its locking state to its unlocking state. This is very easily done and an ejection can therefore be caused even by persons having reduced motoric skills or reduced finger strength, such as children, elderly people or disabled people.

The invention claimed is:

1. An injection device (1) comprising a housing (8),
   a piston rod that is separate element distinct from the housing and wherein the piston rod moves relative to the housing;
   a resilient member (7) adapted to provide a force in the axial direction of the injection device (1), the force being necessary for ejecting a dose from the injection device (1), and
   a dose setting member (2) operatively connected to a dose indicator barrel (4) positioned within the housing (8), the dose setting member (2) and the dose indicator barrel (4) being movable relative to each other and cooperating to set the dose to be ejected from the injection device (1), the
   dose indicator barrel (4) engaging a threaded portion of the housing (8), wherein the dose indicator barrel (4), both during dose setting and during injection, is adapted undergo a combined rotational and translational movement within the housing (8) and relative to the housing (8).
   a dose setting member (2) operatively connected to a dose indicator barrel (4) positioned within the housing (8), the dose setting member (2) and the dose indicator barrel (4) being movable relative to each other and cooperating to set the dose to be ejected from the injection device (1), the dose indicator barrel (4) engaging a threaded portion of the housing (8),
   wherein the dose indicator barrel (4), during dose setting, is adapted undergo a combined rotational and translational movement within the housing (8) and relative to the housing (8).

2. An injection device (1) according to claim 1, wherein the dose setting member (2) engages the dose indicator barrel (4), the injection device (1) further comprising
   a piston rod (5) having a threaded outer surface with a drive track (21) arranged in a longitudinal direction of the outer surface of the piston rod (5),
   a drive member (6) engaging at least part of the drive track (21) of the piston rod (5) and having a threaded inner surface (10) cooperating with a threaded portion (9) arranged on an outer surface of the dose indicator barrel (4), the drive member (6) being adapted to drive and rotate with the piston rod (5) during ejection of a dose from the injection device (1)
   wherein the housing (8) has a threaded portion (14) cooperating with the threaded outer surface of the piston rod (5) so that rotation of the piston rod (5) results in an axial movement of the piston rod (5).

3. An injection device (1) according to claim 1, wherein the dose setting member (2) engages the dose indicator barrel (4), the injection device (1) further comprising
   a piston rod (5) having a threaded outer surface with a track arranged in a longitudinal direction of the outer surface of the piston rod (5),
   a drive member (6) having a threaded portion cooperating with the threaded outer surface of the piston rod (5), and having a threaded inner surface (10) cooperating with a threaded portion (9) arranged on an outer surface of the dose indicator barrel (4), the drive member (6) being adapted to rotate relative to the piston rod (5) during ejection of a dose from the injection device,
   wherein the housing (8) engages at least part of the track of the piston rod (5) so that rotation of the drive member (6) results in an axial movement of the piston rod (5).

4. An injection device (1) according to claim 1, further comprising
   a piston rod (5) having a threaded outer surface with a drive track (21) arranged in a longitudinal direction of the outer surface of the piston rod (5),
   a resilient member housing being at least partly defined by the dose indictor barrel (4) in combination with a main member (15), the dose indicator barrel (4) and the main member (15) being movable in relation to each other, the main member (15) having a threaded portion cooperating with the threaded outer surface of the piston rod (5),
   a drive member (6) operatively connected to the main member (15) via a toothing (19) so that the drive member (6) is movable in relation to the main member (15) during dose setting but rigidly connected to the main member (15) during ejection of a dose from the injection device, the drive member (6) engaging at least part of the drive track (21) on the outer surface of the piston rod (5),
   wherein the housing (8) has a threaded portion (14) cooperating with the threaded outer surface of the piston rod (5) so that rotation of the piston rod (5) by the drive member (6) results in an axial movement of the piston rod (5).

5. An injection device according to claim 4, further comprising an intermediate part (16) engaging the dose setting member (2) and the main member (15) of the resilient member housing, the intermediate part (16) being adapted to provided a biasing force to the drive member (6) in a direction towards the toothing (19).

6. An injection device (1) according to claim 1, further comprising
- a piston rod (5) having a threaded outer surface with a drive track (21) arranged in a longitudinal direction of the outer surface of the piston rod (5),
- a resilient member housing being at least partly defined by the dose indictor barrel (4) and a main member (15),
- a drive member (6) operatively connected to the main member (15) via a toothing (19) in such a way that the drive member (6) is movable in relation to the main member (15) during dose setting but rigidly connected to the main member (15) during ejection of a dose from the injection device, the drive member (6) having threaded portion cooperating with the threaded outer surface of the piston rod (5), wherein the housing (8) engages at least part of the track of the piston rod (5) so that rotation of the drive member (6) results in an axial movement of the piston rod (5).

7. An injection device according to claim 2, further comprising a locking member (11) adapted to fixate the piston rod (5) in such a way that no relative rotation of the piston rod (5) and the housing (8) is possible when the locking member (11) is in its locking position.

8. An injection device according to claim 7, further comprising a release button adapted for releasing the locking member (11) from its locking position.

9. An injection device according to claim 8, wherein the release button is positioned in the distal half of the length of the injection device.

10. An injection device according to claim 3, further comprising a locking member (11) adapted to fixate the drive member (6) in such a way that no relative rotation of the drive member (6) and the housing (8) is possible when the locking member (11) is in its locking position.

11. An injection device according to claim 10, further comprising a release button adapted for releasing the locking member (11) from its locking position, the release button being adapted to be released by a user of the injection device.

12. An injection device according to claim 11, wherein the release button is positioned in the distal half of the length of the injection device.

13. An injection device according to claim 1, wherein the resilient member (7) comprises a helical spring arranged coaxially with the piston rod (5).

14. An injection device (1) comprising
- a housing (8),
- a piston rod for moving axial with respect to the housing, the piston rod being a separate element from the housing, the piston rod being adapted to act upon a cartridge and expel medication from the cartridge;
- a resilient member (7) adapted to provide a force in the axial direction of the injection device (1), the force being necessary for ejecting a dose from the injection device (1), and
- a dose setting member (2) operatively connected to a dose indicator barrel (4) positioned within the housing (8), the dose setting member (2) and the dose indicator barrel (4) being movable relative to each other and cooperating to set the dose to be ejected from the injection device (1), the dose indicator barrel (4) threadedly engaging a threaded portion of the housing (8), wherein the dose indicator barrel may be rotate with respect to the threaded portion of the housing and wherein threaded engagement between the threaded portion of the hosing and the dose indicator barrel causes the dose indicator barrel to translate with respect to the housing when it is rotated the rotation causes the dose indicator, wherein the dose indicator barrel (4), during dose setting, is adapted undergo a combined rotational and translational movement within the housing (8) and relative to the housing (8).

\* \* \* \* \*